United States Patent

Meyer et al.

4,014,207

Mar. 29, 1977

[54] SECTOR SCANNING ULTRASONIC INSPECTION APPARATUS

[75] Inventors: Edward P. Meyer, Boulder; William L. Wright, Longmont, both of Colo.

[73] Assignee: Picker Electronics, Inc., Northford, Conn.

[ * ] Notice: The portion of the term of this patent subsequent to Dec. 9, 1992, has been disclaimed.

[22] Filed: Apr. 28, 1975

[21] Appl. No.: 572,058

Related U.S. Application Data

[60] Division of Ser. No. 62,143, Aug. 7, 1970, Pat. No. 3,924,452, which is a continuation of Ser. No. 801,882, Oct. 1, 1968, abandoned, which is a continuation-in-part of Ser. No. 373,312, June 8, 1964, abandoned.

[52] U.S. Cl. .................................... 73/67.8 S
[51] Int. Cl.² ................................... G01N 29/04
[58] Field of Search ................. 73/67.7–67.9, 73/71.5

[56] References Cited

UNITED STATES PATENTS

| 3,086,390 | 4/1963 | Brown | 73/67.8 |
| 3,257,843 | 6/1966 | Cowan | 73/71.5 |
| 3,308,652 | 3/1967 | Appel et al. | 73/67.8 X |

OTHER PUBLICATIONS

Buchanan, et al., Ultrasonic Flaw Plotting Equipment—A New Concept For Industrial Inspection, Non-Destructive Testing, Sept.–Oct., 1955, pp. 17–25.
Buchanan, et al., Watertown Arsenal Laboratory, No. Wal 143128, July, 1955, pp. 1 & 12–16.

*Primary Examiner*—Richard C. Queisser
*Assistant Examiner*—John P. Beauchamp
*Attorney, Agent, or Firm*—Watts, Hoffmann, Fisher & Heinke Co.

[57] ABSTRACT

This is an ultrasonic transducer scanning support system comprising at least three arms serially joined in pivotal relation one to the other and to a base. Three position transponders are mounted on the base with each of the pivoted arms operatively coupled to a transponder whereby signals are developed representative of the position of a transducer mounted on the end of the third arm which control the origin of an indicating means to correspond to the position of the transducer.

10 Claims, 13 Drawing Figures

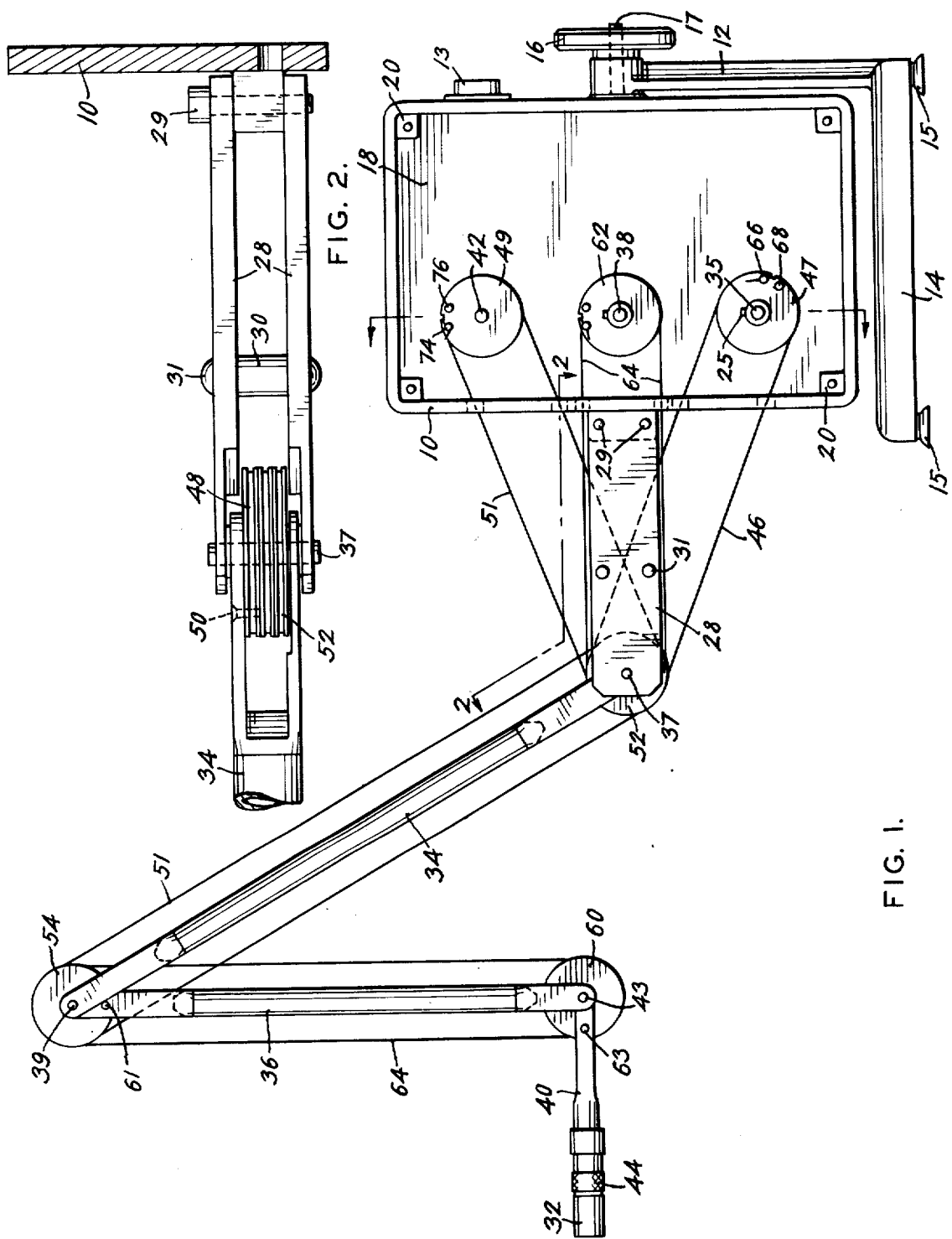

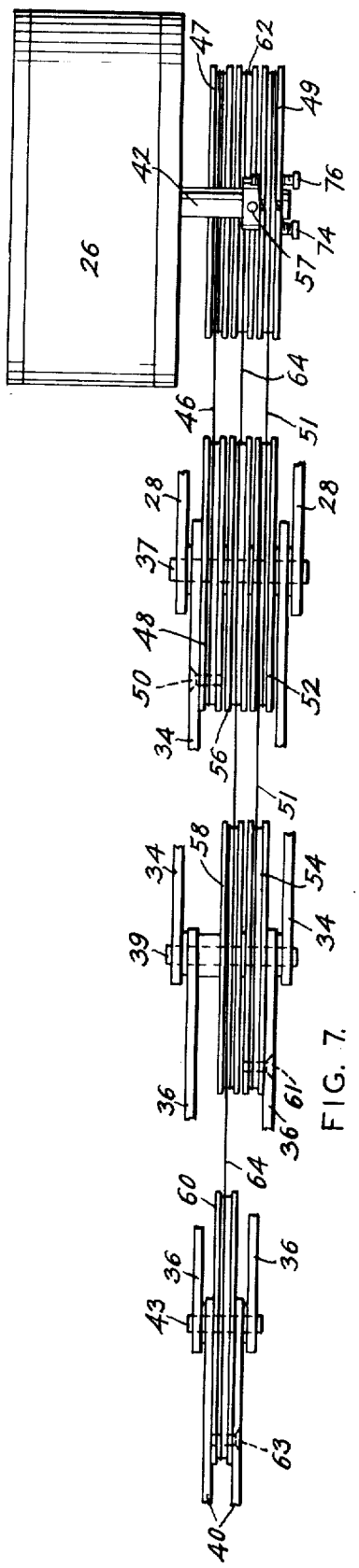
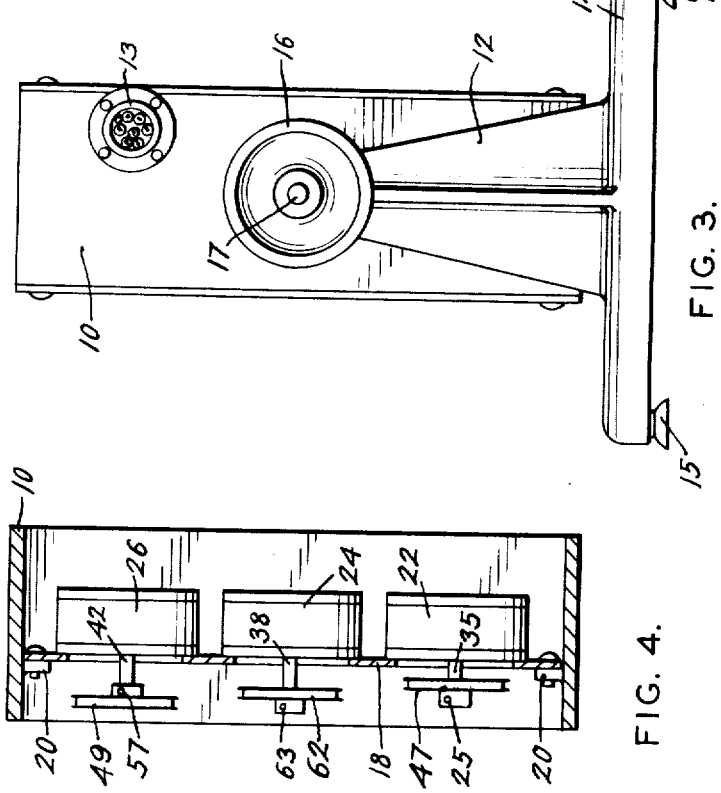
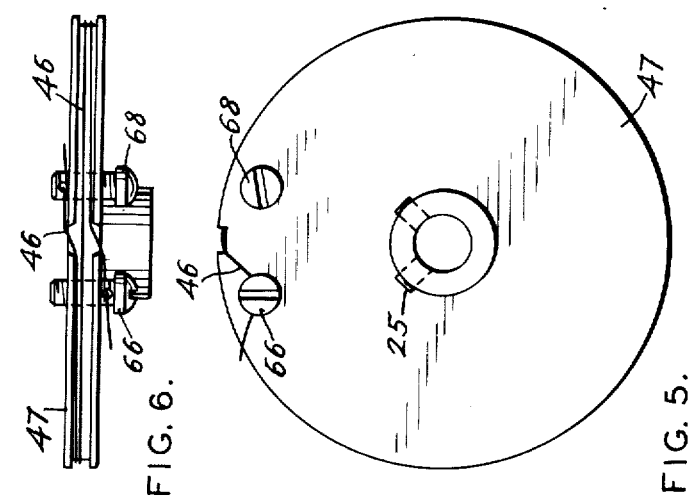
FIG. 3.
FIG. 4.
FIG. 5.
FIG. 6.
FIG. 7.

SECTOR SCANNING ULTRASONIC INSPECTION APPARATUS

This application is a division of application Ser. No. 62,143, filed Aug. 7, 1970, now U.S. Pat. No. 3,924,452, which is a continuation of application Ser. No. 801,882, filed Oct. 1, 1968, abandoned, which is a continuation-in-part of application Ser. No. 373,312, filed June 8, 1964, abandoned.

The present invention uses ultrasonic techniques closely related to the echo-ranging techniques developed in the field of sonar during and after World War II. Ultrasonic echo-ranging devices normally include a generator for producing ultrasonic energy, a transducer for applying vibrational energy to a medium of transmission and receiving energy echoed back through that medium, a receiver for amplifying and detecting the echoed energy, an indicating unit for displaying the echoed information and a control (synchronizing) unit for synchronizing the action between transmitter and receiver.

The present invention is also related to non-destructive testing (NDT), which is the inspection of the surface or interior of a solid object without destroying the object. X-rays and gamma rays are also used in certain types of such testing, but such rays are electromagnetic and hence can penetrate only limited distances into metal.

Ultrasonic visualization techniques are being increasingly used for non-destructive testing and in particular for medical diagnosis. The approach used in medical diagnosis is basically similar to those used in non-destructive testing and echo-ranging. The transducer is applied to the area under investigation, pulses of ultrasonic energy are applied, and reflected pulses (echoes) are detected and displayed on a cathode ray tube.

Ultrasonic examinations are possible in areas where X-ray examinations are either inconclusive or inadvisable, such as in examinations of the cranium and eyes. By studying the displayed data, the examining physician can distinguish between normal and abnormal tissues. These ultrasonic techniques have been found useful in detecting cancers, and other tumors in the brain, breast and heart. For the study of organs like the liver, kidney, spleen, pancreas and breast, and for study of fluid-filled structures like the bladder, stomach and pregnant uterus, ultrasonics will give pictorial anatomical and pathological information not obtainable by X-ray.

The apparatus and methods heretofore available have had some serious disadvantages principally in terms of resolution of the objects under observation and the degree of skill required by the operators. Also, in the past most ultrasonic equipment required that the object being investigated be placed in a fluid bath during actual investigation.

It is an important object of the present invention to provide an improved arrangement for the utilization of ultrasonic energy in non-destructive testing and a method of using it which overcomes some or all of the disadvantages of prior art devices.

Another important object of the present invention is to provide for improved scanning of the object under investigation to provide greater resolution.

A further object of the present invention is to avoid the necessity of immersion of the object during the investigation procedure.

A still further object of the present invention is to provide an improved scanning arrangement which automatically relates the positioning of the ultrasonic transmitter and receiver with the image produced on a read-out device, such as a cathode ray tube.

Still another object of the present invention is to provide a scanner of improved design for use with apparatus utilizing ultrasonic principles which permits rocking the transducer to provide improved resolution of internal aspects of a solid body.

Other objects and a fuller understanding of the invention may be had by referring to the following description and claims, taken in conjunction with the accompanying drawings, in which:

FIG. 1 is a side elevational view of the scanner portion of ultrasonic equipment constructed in accordance with the principles of the present invention;

FIG. 2 is a top view of the structure illustrated in FIG. 1 taken in planes substantially indicated by lines 2—2;

FIG. 3 is a rear elevational view of the equipment illustrated in FIG. 1;

FIG. 4 is a transverse sectional view of the structure illustrated in FIG. 1 taken along the lines 4—4;

FIG. 5 is a side elevational view of a single one of the pulleys illustrated in FIG. 1;

FIG. 6 is a top view of the pulley illustrated in FIG. 5;

FIG. 7 is a diagrammatic top view of the linkage system with certain portions cut away to show the outermost connection of the apparatus with the potentiometers;

Figure 9:
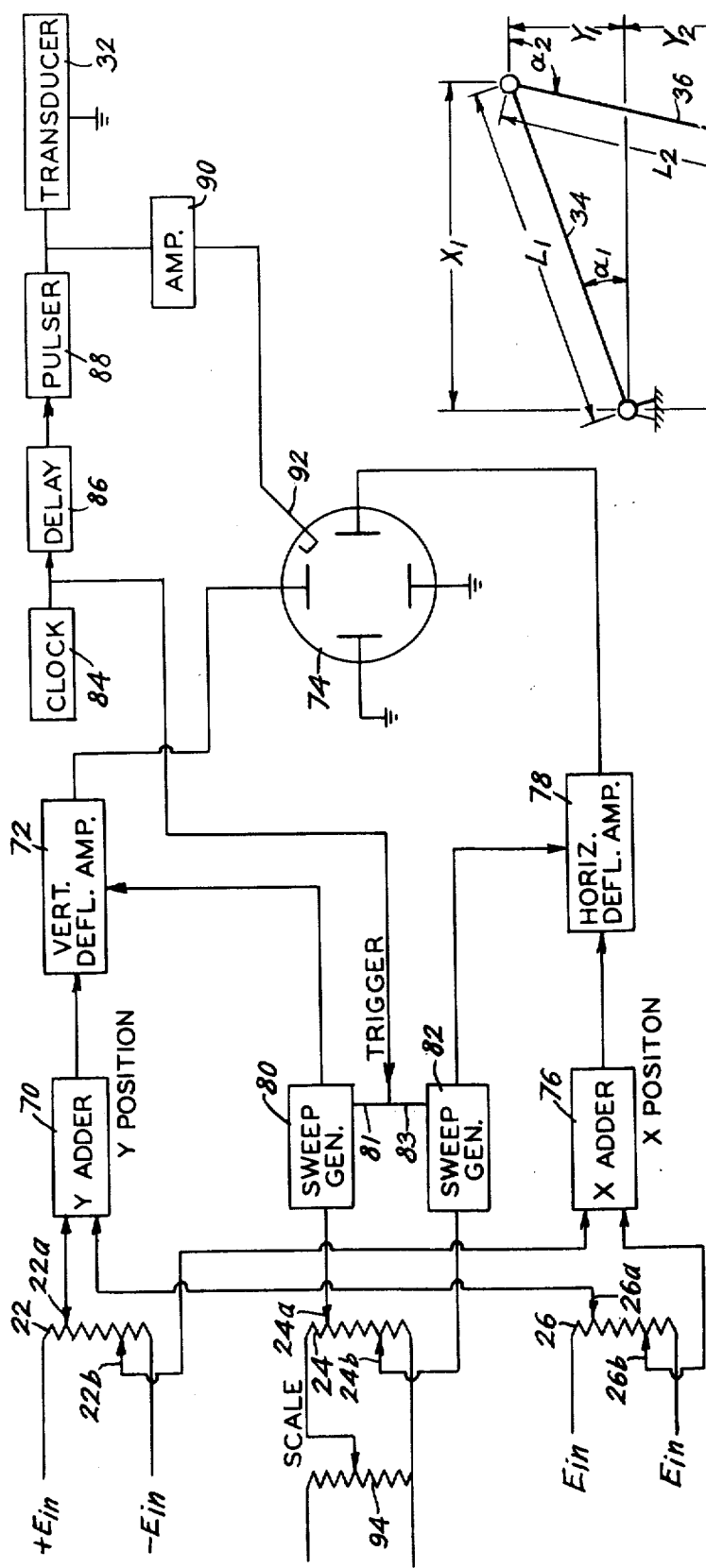
FIG. 9 is a schematic diagram of one embodiment of electric circuitry of the apparatus.

In accordance with the present invention, there is provided apparatus including a transducer for sending ultrasonic signals through an object under investigation and for receiving signals reflected back thereto, and a device for translating the reflected signals into a suitable reproduction of the object being investigated. The apparatus includes a scanning arrangement, which comprises a base having a support mounted thereon for pivotal movement, a series of arms successively and adjustably connected to each other having one end of the first of the successively connected arms mounted on the support and having an ultrasonic transducer mounted at the end of the last of the successively and adjustably connected arms. A series of potentiometers are operatively connected to the adjustable arms upon which the transducer is mounted, the potentiometers being adapted to develop signals representative of the positioning of the arms. Means are provided for transmitting the developed signals to the translating device for translating the position and attitude of the source of ultrasonic signals into a suitable reproduction which is properly oriented with respect to the object being investigated.

With reference to the drawing and, in particular, to FIGS. 1, 2, 3 and 4, a system embodying the invention includes a frame 10, having its rear surface mounted on a rear vertical element 12 of a support 14 provided with feet 15, which may be optional. A screw wheel 16 is threaded onto a bolt 17 which passes through the upper portion of the rear vertical element 12 and is attached to the frame 10 to permit positioning of the frame 10 in any desired angular position about the axis of the bolt 17. A center plate 18 is mounted interiorly of the frame 10 on mounting lugs 20. Positioned on the center plate 18, one above the other, are three sine-cosine potentiometers indicated generally from bottom to top as 22, 24 and 26. The slider of each potentiometer is operatively coupled through a mechanical linkage to a transducer 32 to provide electrical signals representative of the position of the transducer as will be later described.

A pair of spaced parallel arms 28 extend horizontally from the front of the frame 10 and are mounted thereon at one end by bolts 29. The arms are held in spaced-apart relation by spacers 30 and studs 31. An electrical plug connection 13 is located on the back of the frame 10 through which electrical power is supplied generally to the device, and through which ultrasonic signals are supplied to and taken from the transducer 32. The frame 10 may be selectively positioned about a horizontal axis passing through the bolt 17 by loosening the screw wheel 16, repositioning the frame and tightening the screw wheel.

Figure 8:
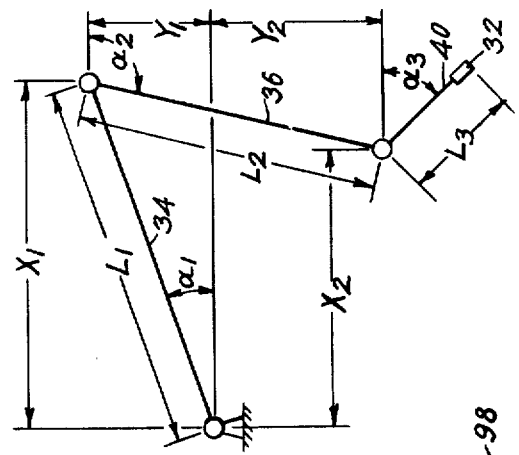
FIG. 8 is a mechanical diagrammatic view of the ultrasonic apparatus illustrated in FIG. 1.

The system by which the movement of the transducer 32 is translated into electrical signals will now be described. Referring particularly to FIGS. 1 and 8, it will be noted that the system contains three interconnected arms 34, 36 and 40. The first arm 34 is bifurcated at each end, with one bifurcated end pivotally connected to the arms 28 by means of a shaft 37. The other bifurcated end of the first arm 34 is similarly pivotally connected to a bifurcated end of the second arm 36 by means of a shaft 39. The other end of the second arm 36 is also bifurcated and pivotally attached to a similarly bifurcated end of the third arm 40 by means of a shaft 43. The transducer 32 is attached to the opposite side of the third arm 40 by a screw connector 44, which includes a plug and socket for electrical connections (not shown). It is now readily seen that the first arm 34 pivots about the axis of the shaft 37. The second arm 36 being pivoted to the first arm 34 and the third arm 40 being pivoted to the second arm 36 permits the transducer to describe almost a complete circle. The pivotal connections of the first and second arms 34 and 36 respectively permit the positioning of the end of the second arm at almost any point within a plane normal to the axes of the shafts 37, 39, 43. The third arm 40 being pivoted to the second arm 36 in effect may pivot about any point in a plane limited only by the total motion of the first arm 34 and the second arm 36. The third arm 40 permits freedom of angular position of the transducer 32 allowing the transducer 32 to be placed at any position in the plane and its axis aligned at any angle within its limits. Furthermore, since the frame 10 can be rotated about a horizontal axis at right angles to the axes of the pivoting arms 34, 36 and 40, the inspection plane can be adjusted substantially to any desired angle.

The transducer 32 in being positioned to scan the object or individual under investigation moves the sliders of the potentiometers 22, 24 and 26 mounted on the frame 10 to correspond to such positioning. The potentiometers translate the movement of the transducer into electrical signals which are applied to a readout device, such as a cathode ray tube (CRT), for displaying the desired internal structure of the subject under investigation upon the screen of the tube.

Referring now to FIGS. 4, 5 and 6, it will be seen that the potentiometers 22, 24 and 26, which are of the sine-cosine type, are mounted on the center plate 18 of the frame 10 one above the one. The potentiometers 22, 24, 26 have sliders respectively mounted on shafts 35, 38, 42, which are adapted to be adjusted in such a manner as to provide signals on the sliders that correspond to trigonometric functions of the respective angles formed between the arms 34, 36 and 40 and the horizontal. The potentiometer shafts extend through openings in the plate 18. The shafts 35, 38, 42 respectively have pulleys 47, 62 and 49 securely mounted thereon and held in position by screws 25, 63 and 57 respectively.

Again referring to the drawings in general but, in particular, to FIGS. 1, 2 and 7, the structure and operations relative to the manner of actuating the potentiometers and producing a suitable reproduction of the object under investigation will now be discussed. It is seen that a pulley 48 is pivotally mounted on the shaft 37 at the pivotal position of arm 34 and within the bifurcations of arm 34 and the parallel arms 28. The pulley 48 is fixedly connected to the arm 34 by pin or screw 50 and rotates with the arm 34 about the shaft 37. A belt 46, which may take the form of a steel wire, is passed around each of the pulleys 47, 48, thus providing a driving connection between the potentiometer 22 and the arm 34 in such a manner as to allow a proportional rotation between the potentiometer 22 and the arm 34, which may conveniently have a one-to-one relation. Screws 66 and 68 provided near the periphery of the pulley 48 receive the ends of the belt 46 in a manner to permit the tensioning of the belt 46 over the pulleys. Thus it is seen that the potentiometer 22 is mechanically coupled through the pulleys 47 and 48, the belt 46, and the screw 50 to the arm 34.

The potentiometer 26 has a pulley 49 attached to its shaft 42 by a screw 57 and is driven by a belt and pulley arrangement in a manner to be mechanically coupled to the arm 36. The potentiometer 26 is connected to the arm 36 through a belt 51 which passes around the pulley 49 over a second pulley 52 which acts as an idler pulley mounted for free rotation on the shaft 37. The pulley 52 is not directly connected with the first arm 34 and does not rotate with movement of that arm. The belt 50 is extended to connect to a pulley 54 mounted on the shaft 39 and fixedly connected to the arm 36 by a pin or screw 61. Since the pulley 54 is directly connected to the arm 36, movement of the arm 36 about the axis of the shaft 39 is, of course, transmitted through the belt 51, the idler pulley 52 and the pulley 49 to the shaft 42 of the potentiometer 26, but no motion of the potentiometer shaft 42 will occur as a direct result of movement of the arm 34. Screws 74 and 76 are provided on the pulley 49 to provide for tensioning and holding the belt 51.

The third potentiometer 24 is arranged to be responsive to angular movement of the third or transducer arm 40. An idler pulley 56 is mounted for free rotation on the shaft 37 in the same manner as the pulley 52. Another idler pulley 58 is similarly mounted for free rotation on the shaft 39. A pulley 60 is mounted on the shaft 43 and is directly connected to the third arm 40 by a pin or screw 60'. The pulley 60 is adapted to rotate with the third arm 40 about the axis of the shaft 43. A pulley 62 is mounted on the potentiometer shaft 38 and held by screws 63. A belt 64 is passed around each of the pulleys 56, 58, 60, 62 in a conventional manner to provide a driving connection between the third arm 40 and the shaft 38 of the potentiometer 24. The belt 64 may be conveniently arranged to pass continuously over the four pulleys by using additional turns as necessary at each pulley. Since the pulley 60 is directly connected to the transducer arm 40, angular movement of the arm 40 about the axis defined by the shaft 43 is transmitted to the shaft 38 of the potentiometer 24. Thus, it is apparent that upon variation of the positions of the arms 34, 36, and 40, the involved belt and pulley arrangements will cause the positions of sliders of the three potentiometers 22, 24, 26 to be varied to correspond with the angular positions of the respective arms.

In order to better understand the operation of applicants' invention, attention is further directed to FIG. 9, which is a partially block and partially schematic diagram of the electrical circuitry of apparatus embodying the invention. As is well-known in the art, ultrasonic waves may be appropriately generated by driving a transducer by applying there to an electrical signal having a frequency in the ultrasonic range. The transducer normally includes a transducer element which may be composed of barium titanate or lithium sulfate. However, it may be also composed of other materials displaying piezoelectric or magnetostrictive characteristics. The ultrasonic energy waves generated are then beamed into the object under investigation. When the ultrasonic waves contact areas of varying density within the investigated object, echoes are reflected back from the interfaces to the transducer where they generate electrical signals. The signal directed into the object under investigation and reflected back to the transducer from surfaces and interfaces may be applied to the Z axis input of an oscilloscope to modulate the electron beam intensity and produce a visible pattern of the echo signals received imposed on a time base or sweep. The speed of the sweep is generally one-half that of the ultrasonic wave in the body being examined to take into account the time of travel to and from an echo-producing density variation and thus produce a full distance scale representation on the face of the oscilloscope. When the transducer is positioned against the surface of the object under investigation, the signal applied thereto from the generator is immediately reflected from that surface, thus identifying the position of the transducer and the point of origin of the trace on the readout device. As echoes are received and displayed, the relative positioning is also established. By using a cathode ray tube having a long time-persistence phosphor, these signals will remain for a period of time sufficient to permit the production of a permanent photographic record or, if desired, then can be fed to a storage tube or the like for future reference.

It has been found that markedly increased resolution of the internal structure of a body is obtained when the beam of ultrasonic energy is injected into the body from a source located at the surface of the body and the beam is pivoted about its point of introduction to cover an angular field or sector within the body. Multiple sector scans of the body are obtained by scanning from several points on the body surface. The present invention relates to a method of multiple sector scanning of a body under investigation using ultrasonic techniques and with apparatus for practicing the method.

To facilitate ease of use, the transducer or transmitter needs to have wide latitude of movement. Indications of this movement needs to be impressed on a readout device to permit the operator at all times to be able to correlate the position of the transducer or source of the ultrasonic energy beam with the position of the image or data appearing on the readout device. To facilitate the description of the system in accordance with the present invention that accomplishes that result, reference is made to FIG. 8, which schematically represents the pivoted suspension system of FIG. 1. As previously indicated, the two arms 34, 36 are respectively mechanically coupled to the potentiometers 22, 26, which potentiometers serve to provide signals indicative of the location of the pivot point of arm 40 (the shaft 43) with respect to the fixed pivot point defined by the shaft 37.

To locate the shaft 43, reference axes X and Y are chosen that pass through the axis of the shaft 43. The coordinates of the position of the axis of the shaft 43 are (algebraically):

$$x = x_1 + x_2 \tag{1}$$

where $$x_1 = L_1 \cos\alpha_1$$

$$x_2 = L_2 \cos\alpha_2$$

Thus, $$x = L_1 \cos\alpha_1 + L_2 \cos\alpha_2 \tag{2}$$

where $L_1$ and $L_2$ are the lengths of arms 34 and 36, and $\alpha_1$ and $\alpha_2$ are the angles made thereby with the horizontal $x$ axis.

Also, $$y = y_1 + y_2 \tag{3}$$

where $$Y_1 = L_1 \sin\alpha_1$$

$$Y_2 = L_2 \sin\alpha_2$$

Thus, $$y = L_1 \sin\alpha_1 + L_2 \sin\alpha_2 \tag{4}$$

The potentiometers 22, 26 and 24 are each of a well-known type that provides two electrical output signals whose amplitudes correspond to sine and cosine trigonometric functions of the rotational position of the shaft of the potentiometer. A suitable potentiometer is known as a Model 303, available from Computer Instruments Corporation, Hempstead, New York. With the arrangement shown, if equal positive and negative voltages are applied across a potentiometer, then the output may change polarity from positive to negative as the angle of the shaft changes. Thus, if $+E_{in}$ and $-E_{in}$ volts are applied across the potentiometer 22, the sine and cosine outputs from the sliders 22a and 22b, respectively are $$E_{\mu l} \text{ out} = E_{1 l_n} \sin\alpha_1 \tag{5}$$

and $$E_{x1} \text{ out} = E_{1in} \cos \alpha_1 \qquad (6)$$

where $\alpha_1$ is the angle of rotation of the shaft connecting the two sliders 22a, 22b with respect to the reference position, which is the same as the angle $\alpha_1$ shown in FIG. 8. A corresponding relationship exists for the potentiometer 26 and its sliders 26a, 26b with respect to the angle $\alpha_2$.

When the corresponding arm 34, 36, 40 controlling a potentiometer 22, 26, 24 is horizontally extended, the output from the sine slider a is zero, and the output from the cosine slider b is maximum positive; when the corresponding arm is turned horizontally inwardly, the a output is again zero, and the b output is maximum negative. Both the sine and cosine functions are thus obtainable from two sliders of each potentiometer, or may be obtainable by other means as known in the art.

To provide for the proper voltage output ratio from the potentiometers 22 and 26 in terms of positions of the axes of the shafts 39, 43, the voltages impressed across the potentiometers 22 and 26 are in the same ratio as the respective lengths of the arms 34 and 36, or $$E_{1in}/L_1 = E_{2in}/L_2 \qquad (7)$$

Thus, conversion means are provided for converting the positions of the axes of the shafts from polar to rectangular coordinates.

Now the position of the shaft 43 with respect to the x, y axes may be obtained in accordance with the relationship $$E_x \text{ out} = E_{x1} \text{ out} + E_{x2} \text{ out} \qquad (8)$$

and $$E_y \text{ out} = E_{y1} \text{ out} + E_{y2} \text{ out} \qquad (9)$$

where $E_x$ out $= Kx$ $E_y$ out $= ky$ and constant $K$ has dimensions of volts per unit length.

Again referring to FIG. 9, the $E_{y1}$ out and $E_{y2}$ out voltages from the sine function sliders 22a, 26a of the potentiometers 22, 26 are fed to a Y adder 70 and the sum output of the adder 70 is fed to a vertical deflection amplifier 72 for driving vertical deflection plates of a cathode ray tube 74. In like manner, the $E_{x1}$ out and $E_{x2}$ out voltages from sliders 22b, 26b of the potentiometers 22, 26 are fed to an X adder 76 and the sum output of the adder 76 is fed to a horizontal deflection amplifier 78 for driving horizontal deflection plates of the cathode ray tube 74. These voltages establish the origin of the scan of the electron beam on the face of the tube and, by adjustment of positioning controls of the oscilloscope, the spot can be positioned as desired at any point or off the face of the tube. The spot may not be visible as the beam may be biased to cut-off to be visible only when a signal of the correct polarity is applied to a Z axis or intensity control electrode 92 of the cathode ray tube 74.

The potentiometer 24, which is coupled to and actuated by the movement of the arm 40 carrying the transducer 32, provides electrical signals representative of the angular positioning of the arm 40 with respect to the horizontal. Thus, the angle made by the arm 40 determines also the direction of the beam of ultrasonic energy provided from the transducer 32. A signal is developed at a slider 24a of the potentiometer 24 which is representative of the sine function of the angle $\alpha_3$ (FIG. 8) with respect to the horizontal, which signal is fed to the sweep generator 80. The sweep generator 80, upon receiving a pulse on a trigger input 81, develops an output, usually of the sawtooth type, the time rate of rise of which is governed by the amplitude of the signal from the sine function slider 24a. In a similar manner, a signal is developed at a slider 24b, which is representative of the cosine function of the angle $\alpha_3$ with respect to the horizontal. This signal is fed to a sweep generator 82, which develops a sawtooth output signal in response to a signal on its trigger input 83. The time rate of rise of the sawtooth signal is governed by the amplitude of the signal from the cosine function slider 24b.

The output signal from the sweep generator 80 is fed to the vertical deflection amplifier 72, and the output from the sweep generator 82 is fed to the horizontal deflection amplifier 78. The combined outputs from the sweep generators 80 and 82 cause the electron beam to be swept across the face of the cathode ray tube 74 and the direction that the path of movement of the electron beam takes is correlated to, and controlled by, the angle $\alpha_3$ of the arm 40.

The sweep generators 80, 82 are triggered by a pulse from a clock generator 84 to start the sweep of the cathode ray tube electron beam. This same pulse is fed to a pulse 88 through delay means 86. The time delay provided by the delay means 86 is sufficient to permit the CRT electron beam to travel a distance equivalent to the distance from the radiating surface of the transducer 32 to the shaft 43 before the transducer is energized, so that the apparent origin of the sweep represents the true position of the shaft 43. This delay is required only where the transducer is in fact displaced from the known position of shaft 43. The transducer 32 is energized by the pulser 88 producing a pulse of ultrasonic energy. The output of the pulser 88 is also fed to the intensity control electrode 92 of the cathode ray tube through an amplifier 90.

It will be seen that the scale or image size will be a function of the magnitude of the deflection voltages applied to the deflection plates of the cathode ray tube 74. By adjusting the voltages applied to the potentiometer 24 by means of a rheostat 94 or other suitable means, the scale of the image may be selected. The scale or size of the image may also be chained by maintaining the input voltage to the potentiometer 24 constant and varying the gain of the deflection amplifiers 72 and 78 as will be understood by those skilled in the art.

In operating the device, the generating surface of the transducer is positioned against the surface of an object under investigation. Each time a clock pulse from the clock 84 reaches the sweep generators, sweep signals of suitable wave forms are produced and applied to the deflection means of the cathode ray tube in accordance with the signals received from potentiometer 24, which reflect the angle $\alpha_3$ that the arm 40 makes with the horizontal. Thus, the electron beam starts to scan across the face of the tube, although it is invisible to the eye. The scan originates at a point which corresponds to the position of the shaft 43 and moves in a direction which corresponds to the angular position of the arm 40; that is, in the direction the ultrasonic beam from transducer 32 is directed. The clock pulse from the clock 84 is also applied to the delay means 86. The clock pulse from the clock 84 is also applied to the delay means 86. After the electron beam has traveled a distance equivalent to the length of the arm 40, the pulser 88 is energized which pulses the transducer 32. The output of the pulser 88 is also amplified by the amplifier 90 and applied to the intensity control electrode of the cathode ray tube and appears on the face thereof as a spot of visible light. The beam of ultrasonic energy is propagated within the body under investigation, and when the beam encounters a change in density within the body, a reflection wave or echo is reflected back to the transducer 32. As a reflection is received, it is amplified by the amplifier 90 and applied to the intensity control electrode 92 of the cathode ray tube so that it appears on the CRT face as a visible spot of light. In the time interval between the original signal generated by the transducer 32 and the reflected signal received, the CRT electron beam will have moved across the face of the tube so that spots representing reflections will occur in spaced relation corresponding to the distance from the surface of the object and the internal anomaly, and in a direction essentially corresponding with the axis of the ultrasonic beam. The repetition rate of the clock 84 is chosen to permit the receipt and storage of the echo signals from a particular object before the generation of a new signal.

Figure 10A:
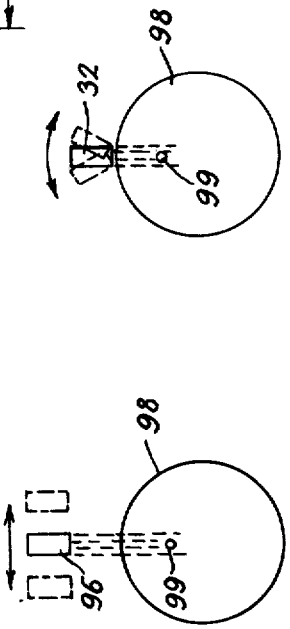
FIGS. 10A and 10B illustrate respectively a typical method of prior art scanning and that of the present invention.
Figure 10B:
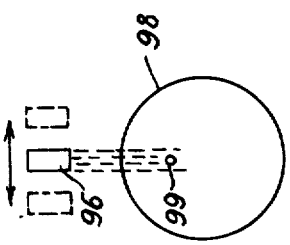

With the system of the present invention, it is possible to carry out a sector scanning of an object from essentially any position and in any plane. Referring to FIGS. 10A and 10B, FIG. 10A depicts the manner in which prior art scanning has been carried out. First, a transducer 96 and an object 98 under investigation are separated usually by water and the transducer is traversed in a straight line manner. A defect 99 within the object 98 is displayed usually upon a cathode ray tube or storage tube. The image has generally had poor resolution. In contrast thereto, the transducer 32 of the present invention is close to the object under investigation (FIG. 10B) and is rocked essentially about a point on the surface of the object. For reasons not yet completely clear, the resolution of an image of a defect 99 in a body 98 is markedly improved over the results obtained with the prior art teachings. It is theorized that the manner of scanning provides greater impingement of waves on the defect, and the device of the invention provides ready access to the information obtained from a body under investigation.

Figures 11, 12:
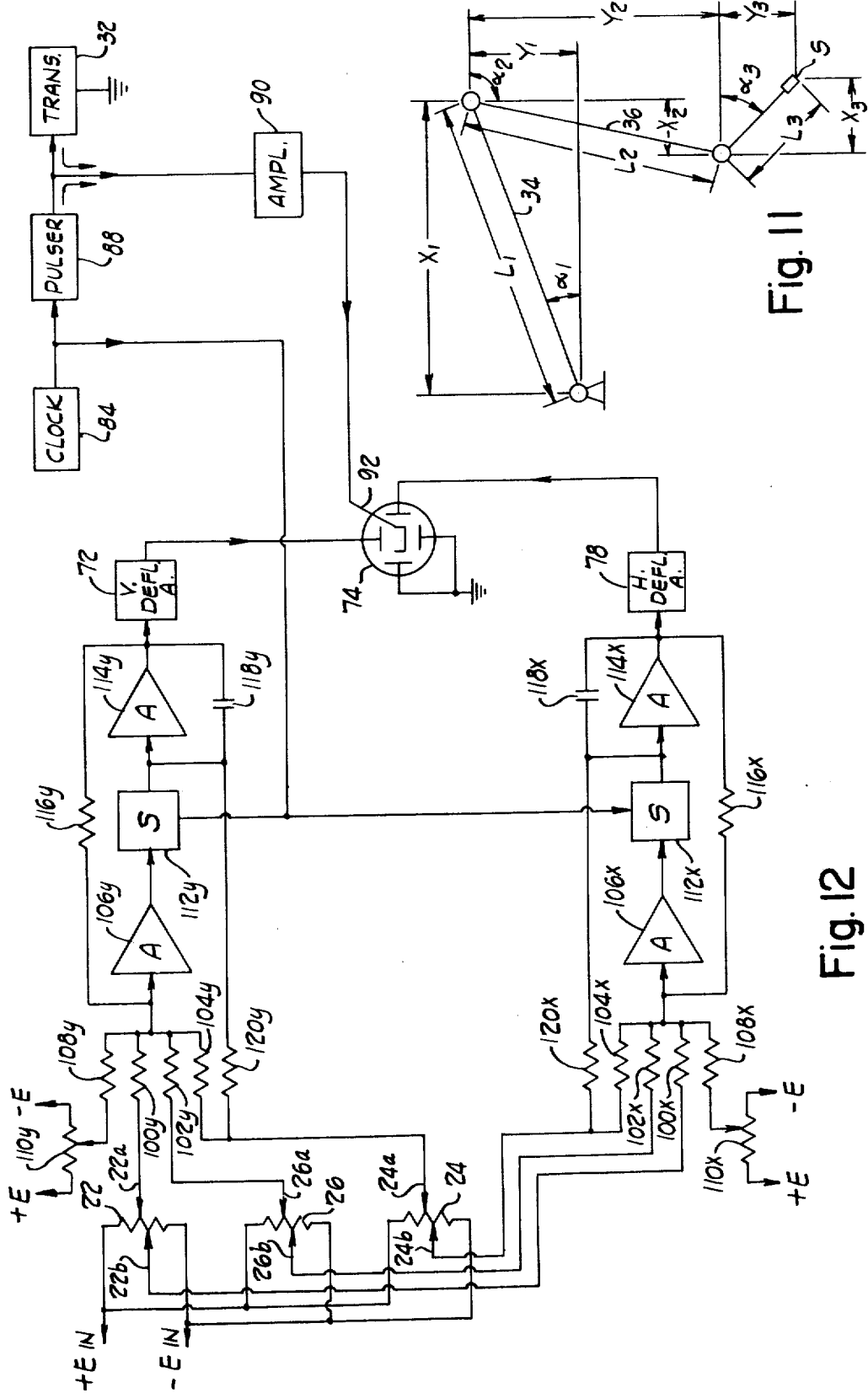
FIG. 11 is another mechanical diagrammatic view of the ultrasonic apparatus shown in FIG. 1, but showing additional definable quantities.
FIG. 12 is a schematic diagram of another embodiment of electronic circuitry of the apparatus that takes into account the additional quantities shown in FIG. 11.

FIGS. 11 and 12 illustrate a modification of the invention, whereby it is possible to locate the position of the transducer 32 exactly in terms of the reference axes X and Y. Thus, the delay 86 shown in FIG. 9 can be eliminated.

Referring now to FIG. 11, it is seen that if $L_3$ and $\alpha_3$ are known, then $$x_3 = L_3 \cos \alpha_3 \tag{10}$$

and $$Y_3 = L_3 \sin \alpha_3. \tag{11}$$

Where $X_1$, $Y_1$, $X_2$, and $Y_2$ are as previously defined, the location of a point S on the face of the transducer 32 (the origin of the ultrasonic pulse) with respect to the X and Y axes becomes $$X = X_1 + X_2 + X_3 = L_1 \cos \alpha_1 + L_2 \cos \alpha_2 + L_3 \cos \alpha_3 \tag{12}$$

and $$y = Y_1 + Y_2 + Y_3 = L_1 \sin \alpha_1 + L_2 \sin \alpha_2 + L_3 \sin \alpha_3 \tag{13}$$

Signals proportional to the sine and cosine functions of the angles $\alpha_1$, $\alpha_2$, $\alpha_3$ are respectively obtained from the potentiometers 22, 26, 24 as previously described.

FIG. 12 illustrates one form of electronic circuitry for accurately positioning origin of the sweep of the beam of the cathode ray tube 74 at a point corresponding to the location of the emitting surface S of the ultrasonic transducer 32. The cathode ray tube beam is then caused to sweep at an angle, as previously described, dictated by the angle $\alpha_3$ representative of the angular positioning of the third or outermost arm 40 that carries the transducer 32.

The embodiment of the invention shown in FIG. 12 differs from that shown in FIG. 9 in that the potentiometers 22, 24, 26 are not energized by voltages that are proportional to the lengths of the arms 34, 40, 36. Rather, the potentiometers are all energized from the same equal positive and negative voltage sources $+E_{in}$ and $-E_{in}$. The X and Y component voltages from the potentiometers are provided separately to passive resistor adder networks as shown in FIG. 12.

Looking first at the Y component positioning and sweep channel, it is seen that the signal representing sin $X_1$ is provided from the slider 22a of the potentiometer 22 to one end of a resistor 100y. Similarly, a signal representing sin $\alpha_2$ is provided from the slider 26a to one end of a resistor 102y, and a signal proportional to sin $\alpha_3$ is provided from the slider 24a to a resistor 104y. The other ends of the resistors 100y, 102y, 104y are connected together and to an input of an operational amplifier 106y. Also connected to the input of the amplifier 106y is one end of a resistor 108y, whose other end is connected to a slider of a potentiometer 110y. The potentiometer 110y is connected between positive and negative voltages +E and −E, and the voltage taken from its movable arm serves as a Y position centering control for the start of the sweep on the cathode ray tube 74.

The output of the operational amplifier 106y is connected through an electronic switch 112y to an input of another operational amplifier 114y. The latter amplifier is part of a sweep generator to provide for vertical or Y deflection of the cathode ray tube beam. To this end, the output of the amplifier 114y is connected to the vertical deflection amplifier 72 to provide positioning and sweep voltages of the proper amplitudes for the cathode ray tube.

A feedback resistor 116y connects the output of the amplifier 114y to the input of the amplifier 106y. An integrating capacitor 118y is connected directly across the amplifier 114y. A resistor 120y is connected from the juncture of the switch 112y and the amplifier 114y to the arm 24a that provides a signal proportional to sin $\alpha_3$. The capacitor 118y and the resistor 120y, acting in conjunction with the switch 112y and the amplifier 114y, provide the vertical or Y axis sweep for the cathode ray tube beam.

It is pointed out that the values of the resistors 100y, 102y, 104y are respectively inversely proportional to the lengths of the arms $L_1$, $L_2$, $L_3$. This feature provides the conversion means necessary so that the input voltages to the amplifier 106y are proportional to X and Y position coordinates. Thus, the voltages supplied to the input of the operational amplifier 106y from the adder network are proportional to $Y_1 + Y_2 + Y_3$, plus a voltage from the potentiometer 110y that is used for centering purposes. These voltages are modified by the voltage developed across the feedback resistor 116y. The voltage provided from the amplifier 106y through the switch 112y to the amplifier 114y is proportional to the Y axis position of the point S on the emitting face of the transducer 32.

While the signal provided from the amplifier 106y determines the origin of the cathode ray tube beam sweep, the signal from the potentiometer arm 24a and the time constant of the capacitor 118y and the resistor 120y determine the vertical sweep speed. The output of the amplifier 114y is a linear ramp (sawtooth) voltage, whose slope is proportional to the sine of $\alpha_3$. $\alpha_3$ is, of course, the angle that the arm 40 carrying the transducer makes with the horizontal.

The fundamental purpose of the switch 112y is to position the cathode ray tube beam at the proper coordinate in the Y direction prior to the start of the sweep. The switch 112y, which is a conventional electronic switch, is opened and closed by pulses received from the clock generator 84. When a pulse is received from the clock generator 84, the switch 112y is closed, so that the output positioning voltages of the amplifier 106y are provided as input voltages to the amplifier 114y. This initially positions the beam of the cathode ray tube at the proper Y coordinate to start the sweep. At the end of the clock pulse, the switch 112y opens and generation of the sawtooth sweep voltage is initiated. This continues until receipt of another clock pulse from the generator 84, at which time the starting point of the sweep in the Y direction is re-positioned if the transducer 32 has been moved in the interim.

The X or horizontal deflection channel comprises components that are identical to those in the Y or vertical channel. Corresponding components in the horizontal channel are identified by the same reference numerals as those in the vertical channel, but are followed by a suffix x rather than y. The only difference between the two channels is that the input signals to the adder network of the x channel are taken from the cosine sliders 22b, 24b, 26b of the three potentiometers rather than from the sine sliders. It is believed that a detailed explanation of the construction and operation of the x channel is not necessary to a full understanding of the invention, in view of the description of the y channel.

The composite output voltage of the vertical deflection amplifier 72 corresponding to the Y position of the transducer surface S and the sine of the angle $\alpha_3$, and the composite voltage from the horizontal deflection amplifier 78 representing the X position of the transducer face S and the cosine of the angle $\alpha_3$ are added vectorially in the electrostatic deflection cathode ray tube 74. This produces a trace on the cathode ray tube face which corresponds completely in position and direction to the path of the ultrasonic beam produced by the transistor 32 in an object under investigation.

Although the invention has been described with a certain degree of particularity, it will be understood that the present disclosure has been made only by way of example and that numerous changes in the details of construction and the combination and arrangement of parts may be resorted to without departing from the spirit and scope of the invention as hereinafter claimed.

We claim:

1. In an ultrasonic apparatus for investigating the internal structure of an object and having electroacoustic transducer for transmitting ultrasonic signals through an object to be investigated and for receiving reflected ultrasonic signals, an ultrasonic generator connected to said transducer, a readout device for translating reflected ultrasonic signals received by said transducer into a visible reproduction of reflections from and within said object being investigated, the combination comprising:
 a. supporting means supporting the electroacoustic transducer for restraining movement of the transducer to emit signals having axes in a single predetermined plane while the transducer is substantially in contact with the surface of said object, said supporting means comprising:
  i. a base;
  ii. a first arm pivotally connected to said base for movement about a first axis transverse to said predetermined plane;
  iii. a second arm pivotally connected to said first arm for movement about a second axis transverse to said predetermined plane; and,
  iv. a third arm pivotally connected to said second arm for movement about a third axis transverse to said predetermined plane, the transducer being connected to said third arm for transmitting and receiving ultrasonic signals having signal axes substantially in said predetermined plane;
 b. first signal generator means responsive to movement of said third arm for providing first electrical signals corresponding to direction of emission of said ultrasonic signals;
 c. second signal generator means responsive to movement of said second and first arms for providing second and third electrical signals respectively related to angular positions of said third and second axes about said second and first axes, respectively;
 d. conversion means responsive to said second and third electrical signals for providing a fourth electrical signal representative of x and y coordinate positions of said transducer; and,
 e. means for transmitting said first and fourth electrical signals to said readout device for producing a visual representation of the location of said transducer and of the direction of emission of said ultrasonic signals from said transducer in said predetermined plane.

2. Apparatus according to claim 1 wherein the conversion means includes means for providing fifth and sixth electrical signals representative of x and y coordinate positions of said first and second axes; and,
 means responsive to the fifth and sixth electrical signals to provide said fourth electrical signal representative of the x and y coordinate positions of the transducer means.

3. The apparatus according to claim 1 wherein the first and second signal generator means each comprise a resolver potentiometer having a rotatable shaft for providing output signals related to two trigonometric functions of rotational position of such shaft.

4. The apparatus according to claim 1 wherein said base is rotatable about a fourth axis to thereby vary angular position of said predetermined plane.

5. The apparatus according to claim 3 and including a plurality of belt and pulley arrangements connecting the first, second and third arms to the rotatable shafts of the first, second and third resolver potentiometers.

6. The apparatus according to claim 1 wherein the readout device comprises a cathode ray tube having deflection means for deflecting an indicator on a display along $x$ and $y$ axes and said first and fourth electrical signals are coupled to the deflection means for varying the origin of said indicator to correspond to the location of the transducer means and for controlling the direction of deflection of the indicator to correspond to the direction of emission of the ultrasonic signals from the transducer means.

7. The apparatus according to claim 1 wherein the conversion means further includes means for respectively energizing the second signal generator means with voltage potentials respectively proportional to lengths of the second and third arms.

8. The apparatus according to claim 1 wherein the first, second and third axis are parallel to each other and are normal to said beam axes.

9. Ultrasonic apparatus for investigating the internal structure of an object comprising:
   a. electroacoustic transducer for transmitting ultrasonic signals through an object to be investigated and for receiving reflected ultrasonic signals;
   b. an ultrasonic generator connected to said transducer;
   c. a readout device for translating reflected ultrasonic signals received by said transducer into a visible reproduction of reflections from and within said object being investigated;
   d. supporting means supporting the electroacoustic transducer for restraining movement of the transducer means to emit signals along signal axes substantially in a single predetermined plane while the transducer is substantially in contact with the surface of said object, said supporting means comprising:
      i. a base;
      ii. a first arm pivotally connected to said base for movement about a first axis transverse to said predetermined plane;
      iii. a second arm pivotally connected to said first arm for movement about a second axis transverse to said predetermined plane; and,
      v. a third arm pivotally connected to said second arm for movement about a third axis transverse to said predetermined plane, the transducer being connected to said third arm for transmitting and receiving ultrasonic signals having axes substantially in said predetermined plane;
   e. first resolver means mounted in association with said base and operatively connected to said third arm for providing first electrical signals corresponding to direction of emission of said ultrasonic signals;
   f. second and third resolver means mounted in association with said base and respectively operatively connected to said second and first arms for respectively providing second and third electrical signals respectively related to angular positions of said third and second axes about said second and first axes, respectively;
   g. conversion means responsive to said second and third electrical signals for providing a fourth electrical signal representative of $x$ and $y$ coordinate positions of said transducer; and,
   h. means for transmitting said first and fourth electrical signals to said readout device for producing a visual representation of the location of said transducer and of the direction of emission of said ultrasonic signals from said transducer in said predetermined plane.

10. In an ultrasonic apparatus for investigating the internal structure of an object having an electro-acoustic transducer having a face for transmitting through an object to be investigated a beam of ultrasonic energy having an axis and for receiving reflected ultrasonic signals, an ultrasonic generator connected to said transducer, a readout device for translating reflected acoustic signals received by said transducer to a visible reproduction of reflections from and within such object, the combination comprising:
   a. a base;
   b. articulated arm structure comprising a plurality of joints and being connected to the base for constrainingly supporting the transducer for rocking movement for rotating the beam while constraining the beam axis substantially in a single plane while the transducer face is in contact with the surface of such subject;
   c. signal generating means operatively associated with the articulated arm structure for producing first and second electrical signals respectively corresponding to direction of emission of said ultrasonic beam and to X and Y coordinate positions of said transducer, said signal generating means including a plurality of resolvers respectively associated with the plurality of joints, one resolver being for monitoring the rocking movement of said transducer for generating the first electrical signal; and
   d. means for transmitting said first and second electrical signals to said readout device for producing a visual representation of the location of said transducer and of the direction of emission of said ultrasonic signals from said transducer means in said predetermined plane.

* * * * *